United States Patent [19]

Flay

[11] 4,035,489

[45] July 12, 1977

[54] DIVALENT METAL SALTS OF O,S-DIALKYL-N-ALKANOYLPHOSPHOROAMIDOTHIOATES

[75] Inventor: Roy B. Flay, Concord, Calif.

[73] Assignee: Chevron Research Company, San Francisco, Calif.

[21] Appl. No.: 714,463

[22] Filed: Aug. 16, 1976

[51] Int. Cl.$^2$ .................. A01N 9/36; C07C 9/24
[52] U.S. Cl. ..................... 424/217; 260/953; 260/959; 424/220
[58] Field of Search ................. 260/950, 953, 959; 424/217, 220

[56] References Cited

U.S. PATENT DOCUMENTS 3,716,600  2/1973  Magee ................. 260/950

Primary Examiner—Anton H. Sutto
Attorney, Agent, or Firm—J. A. Buchanan, Jr.; Dix A. Newell; Raymond Owyang

[57] ABSTRACT

Calcium and barium bis-O,S-dialkyl-N-alkanoylphosphoroamidothioate salts have high insecticidal activity and are substantially more stable than the corresponding O,S-dialkyl-N-alkanoylphosphoroamidothioate compound.

15 Claims, No Drawings

DIVALENT METAL SALTS OF O,S-DIALKYL-N-ALKANOYLPHOS-PHOROAMIDOTHIOATES

BACKGROUND OF THE INVENTION

U.S. Pat. No. 3,716,000, issued Feb. 13, 1973, to P.S. Magee, discloses O,S-dialkyl-N-alkanoylphosphoroamidothioate compounds which have a high degree of insecticidal activity with relatively low mammalian toxicity.

DESCRIPTION OF THE INVENTION

It has now been found that divalent metal salts, particularly calcium and barium salts, of O,S-dialkyl-N-alkanoyl-phosphoroamidothioates are substantially more stable than the corresponding O,S-dialkyl-N-alkanoylphosphoroamidothioate.

The metal salts of the invention are formed from one atom of the divalent metal and two molecules of the phosphoroamidothioate compound. Although the structure of the metal salts is not definitively known, it is considered likely that the new metal salts are salts of the imido tautomeric form of the O,S-dialkyl-N-alkanoylphosphoroamidothioate compound as represented by the following structural formula (I):

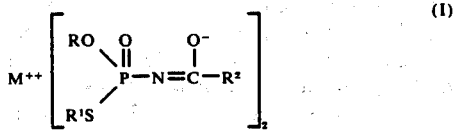

wherein M is calcium or barium, R is alkyl of 1 to 6 carbon atoms, $R^1$ is alkyl of 1 to 6 carbon atoms and $R^2$ is alkyl of 1 to 18 carbon atoms. The $R^2$ group corresponds to the alkyl moiety of the N-alkanoyl group of the phosphoroamidothioate compound.

However, it is appreciated, of course, that in certain environments the new metal salts may be salts of the amido tautomeric form of the O,S-dialkyl-N-alkanoyl-phosphoroamidothioate compound as represented by the following structural formula (II):

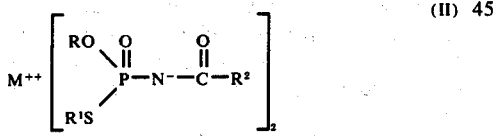

wherein R, $R^1$, $R^2$ and M have the same significance as defined above.

In formulas (I) and (II), R, $R^1$ and $R^2$ individually are preferably lower alkyl of 1 to 3 carobn atoms.

The metal salts are prepared by more-or-less conventional methods.

In one method, a metal hydroxide, e.g., calcium hydroxide, is reacted with the phosphoroamidothioate in the presence of a liquid diluent. Generally, the metal hydroxide and the phosphoroamidothioate are reacted in substantially stoichiometric amounts, i.e., about 1.8 to 2.2 mols of phosphoroamidothioate per one mol of metal hydroxide. Suitable liquid diluents are generally organic solvents in which the phosphoroamidothioate compound is soluble. The reaction temperature is not critical, and generally temperatures from about 25° C to the boiling point of the diluent are satisfactory. Reaction pressure is also not critical, but for convenience the pressure is generally atmospheric. The metal salt is isolated and purified by conventional procedures, e.g., filtraton, crystallization, etc.

In another method, the metal salts are prepared by reacting a metal dihalide, e.g., calcium chloride or barium chloride, with an alkali metal salt, e.g., sodium or potassium, of the phosphoroamidothioate. In this method, the molar ratio of metal halide to alkali metal salt is substantially stoichiometric, e.g., about 1.8 to 2.2 mols of alkali metal phosphoroamidothioate salt per one mol of metal dihalide. The reaction is conducted in a polar organic solvent such as methanol at a temperature from about 25°–100° C. The metal salt product is isolated and purified by conventional procedures.

The alkali metal salts of O,S-dialkyl-N-alkanoylphosphoroamidothioates are believed to be novel compounds and also have insecticial activity. They are prepared by reacting substantially equimolar amounts of an alkali metal carbonate, e.g., sodium or potassium carbonate, with an O,S-dialkyl-N-alkanoylphosphoroamidothioate in the presence of a liquid organic diluent such as methanol or dichloromethane. Suitable reaction temperatures vary from about 25° to 100° C. The reaction pressure may be atmospheric, subatmospheric or superatmospheric. The alkali metal salt product is isolated and purified by conventional procedures.

Representative calcium or barium salts which may be prepared by methods similar to the foregoing methods include:
- calcium bis-(O,S-dimethyl-N-propionylphosphoroamidothioate)
- calcium bis-(O,S-diethyl-N-acetylphosphoroamidothioate)
- calcium bis-(O-methyl-S-ethyl-N-acetylphosphoroamidothioate)
- calcium bis-(O,S-dipropyl-N-decanoylphosphoroamidothioate)
- barium bis-(O,S-dimethyl-N-acetylphosphoroamidothioate), and
- bariumbis-(O,S-diethyl-N-acetylphosphoroamidothioate).

EXAMPLES

Example 1

Calcium salt of O,S-dimethyl-N-acetylphosphoroamidothioate

A mixture of 7.4 g (0.1 mol) calcium hydroxide and 36.6 g (0.2 mol) of O,S-dimethyl-N-acetylphosphoroamidothioate in 200 ml methanol was stirred at 50° C for 2 hours. Infrared analysis of a small sample of the reaction mixture showed that the reaction was complete (no acetyl carbonyl absorption). The reaction mixture was then evaporated under reduced pressure to remove a bout half the methanol, mixed with Cellite filter aid and filtered. LThe filtrate was diluted with 200 ml acetone to precipitate the calcium salt product. The salt was filtered and dried. Eleven g of the salt (a white powder, which melted with decomposition at 220° C) was obtained. Elemental analysis for $C_8H_{18}N_2O_6P_2S_2Ca$ showed: %CA, calc. 9.9, found 9.9; %P, calc. 15.3, found 15.1; %S, calc. 15.8, found 15.6.

The infrared spectrum (nujol mull) of the product showed strong absorption at 6.5 micron (assigned to >C=N< absorption) and at 8.5 micron. The nuclear magnetic spectrum of the product showed the $Ch_3S$—group as a doublet centeed at 2.1 ppm (relative to tetramethylsilane), the $CH_3O$— group as a doublet centered at 3.6 ppm, and the $Ch_3C$-13 group as a doublet centered at 1.95 ppm.

Example 2

Calcium Salt of O,S-dimethyl-N-acetylphosphoroamidothioate

A solution of O,S-dimethyl-N-acetylphosphoroamidothioate was prepared by dissoving 183 g (1.0 mol) of approximately 95% pure O,S-dimethyl-N-acetylphosphoroamidothioate in 2000 ml dichloromethane, mixing the resulting solution with Celete filter aid and filtering. The solution was then diluted with another 1000 ml dichloromethane and vigorously stirred while 37.05 g (1.5 mol) calcium hydroxide was added slowly. After about 15 minutes a gelatinous mixture resulted. The calcium salt product was separated by filtration from mixture, washed with acetone and dried under vacuum. The yield was 187.5 g (97.1% based on 95% pure starting material).

A sample of the salt was converted to O,S-dimethyl-N-acetylphosphoroamidothioate with a cation exchange resin and analyzed by gas-liquid chromatography. The chromatography analysis showed a 95.1% conversion of the salt to the O,S-dimethyl-N-acetylphosphoroamidothioadte.

Example 3

Barium Salt of O,S-Dimethyl-N-Acetylphosphoroamidothioate

A 18.3 g (0.1 mol) sample of O,S-dimethyl-N-acetylphosphoroamidothioate was dissolved in 250 ml dichloromethane and filtered to remove small amounts of insoluble impurities. To the resulting solution was added 9.5 g (0.05 mol) barium hydroxide. The mixture was stirred overnight, filtered, washed with acetone and dried under vacuum to give 24.2 g of the barium salt.

A sample of the barium salt was converted to O,S-dimethyl-N-acetylphosphoroamidothioate with a cation exchange resin. Gas-liquid chromatography analysis showed that the salt was converted to the O,S-dimethyl-N-acetylphosphoroamidothioate in an 84% yield.

Example 4

Preparation of the Sodium Salt of O,S-Dimethyl-N-acetylphosphoroamidothioate

A mixture of 750 g (4 mols) of O,S-dimethyl-N-acetylphosphoroamidothioate and 424 g (4 mols) of sodium carbonate in 3000 ml of methanol was heated at just below reflux temperature for 2 hours. The reaction mixture was filtered to remove some precipitated sodium bicarbonate. The filtrate was evaporated under reduced pressure to give the crude sodium salt. The crude salt was washed with acetone, filtered and dried to give the final product. The infrared spectrum of the salt (nujol mull) showed strong carbonyl absorption at 5.8 microns. Elemental analysis for $C_4H_9NO_3PSNa$ showed: %S, calc. 15.6, found 15.1; %P, calc. 15.1, found 15.5.

Example 3

Stability Study

The calcium salt of O,S-dimethyl-N-acetylphosphoroamidothioate was tested for storage stability by maintaining a 20-g sample of the salt in an oven at 70° C. At regular intervals, samples of the salt were removed and analyzed for decomposition by converting the salt to O,S-dimethyl-N-acetylphosphoroamidothioate with a cation exchange resin and determining the amount of O,S-dimeethyl-N-acetylphosphoroamidothioate by gas-liquid chromatography. For comparison, the storage stability of O,S-dimethyl-N-acetylphosphoroamidothioate and its sodium salt were also determined in the same test. The results are tabulated in Table I.

TABLE I

| | Decomposition During Storage at 70° C | | | | | | |
|---|---|---|---|---|---|---|---|
| | Days | | | | | | |
| Compound | 0 | 7 | 14 | 21 | 28 | 35 | 63 |
| O,S-dimethyl-N-acetyl-phosphoroamidothioate | 0% | 4% | 14% | 100% | — | — | — |
| Sodium salt | 0% | 100% | — | — | — | — | — |
| Calcium salt | 0% | 6% | 9% | 9% | 9% | 9% | 11% |

Example 4

Insecticidal Tests

The metal salts of this invention were tested as follows to illustrate their insecticidal activity. The test results are reported in Table II.

Test Procedures

CABBAGE LOOPER (*Trichoplusia ni*): An acetone solution of the candidate toxicant containing a small amount of nonionic emulsifier was diluted with water to 500 ppm. Cucumber leaf sections were dipped in the toxicant solution and dried. The sections were then infested with cabbage looper larvae. Mortality readings were taken after 24 hours.

AMERICAN COCKROACH (*Periplaneta americana L.*): A 250-ppm acetone solution of the candidate toxicant was placed in a microsprayer (atomizer). A random mixture of anesthetized male and female roaches was placed in a container, and 55 mg of the above-described acetone solution was sprayed on it. A lid was placed on the container. A mortality reading was made after 24 hours. HOUSEFLIES (*Musca domestica L.*): A 500-ppm acetone solution of the candidate toxicant was placed in a microsprayer (atomizer). A random mixture of anesthetized male and female flies was placed in a container and 55 mg of the above-described acetone solution was sprayed on it. A lid was placed on the container. A mortality reading was taken after 24 hours.

TWO-SPOTTED MITES (*Tetramuchus urticae*): An acetone solution of the candidate toxicant containing a small amount of nonionic emulsifier was diluted with water to 40 ppm. Pinto bean leaves which were infested with mites were dipped in the toxicant solution. Mortality readings were taken after 24 hours.

APHIDS (*Aphis gossypii Glover*): An acetone solution of the candidate toxicant containing a small amount of nonionic emulsifier was diluted with water to 40 ppm. Cucumber leaves infested with the cottom aphids were dipped in the toxicant solution. Mortality readings were then taken after 24 hours.

TABLE II

| | % Mortality | |
|---|---|---|
| | Example 1 | Example 2 |
| Cabbage Looper (250 ppm) | 50 | 90 |
| American Cockroach (250 ppm) | 100 | 100 |
| Housefly (500 ppm) | 100 | 100 |
| Mite (40 ppm) | 30 | 0 |

TABLE II-continued

| | % Mortality | |
|---|---|---|
| | Example 1 | Example 2 |
| Aphid (40 ppm) | 100 | 96 |

Example 5

Systemic InsecticideTest

This test was carried out to assess the ability of the calcium salt of Example 1 to be absorbed through the plant root system and translocated to the foliage.

A 10,000-ppm stock solution of the calcium salt and a small amount of a nonionic emulsifier in acetone was prepared. The stock solution was then diluted with water to give a test solution of a desired test concentration. A 40-ml sample of the test solution was used to water 4 inch fiber pots containing cucumber plants. The plants were held in a greenhouse (75–85° F) and watered as needed throughout the test period.

The plants were infested with cotton aphids (*Aphis gossypii*) at various days after treatment with the test solution. Insect mortality was determined after 2 days of insect exposure to the treated plants. Four replications are performed at each test concentration.

For comparison, O,S-dimethyl-N-acetyl-O,S-dialkyl-N-alkanoylphosphoroamidothioate was also tested.

The concentration of the solution used to water the plants, time of insect infestation (days after plants treated with insecticide) and percent insect mortality are tabulated in Table III.

TABLE III

| Compound | Conc.[1] | % Control, Days After Treatment | | | | |
|---|---|---|---|---|---|---|
| | | 2 | 7 | 9 | 14 | 16 |
| Ca salt of O,S-dimethyl-N-acetylphosphoroamidothiote | 40 | 100 | 100 | 100 | 100 | 100 |
| | 16 | 100 | 100 | 100 | 98 | 94 |
| | 6.4 | 100 | 100 | 82 | 61 | 2 |
| O,S-dimethyl-N-acetylphosphoroamidothioate | 40 | 100 | 100 | 100 | 100 | 100 |
| | 16 | 100 | 100 | 77 | 68 | 60 |
| | 6.4 | 100 | 100 | 61 | 44 | 10 |

[1]micrograms/cm$^2$

The metal salts are toxic to a variety of crop and household pests, in addition to the typical pests exemplified above. Like most agricultural chemicals, they are not usually applied full strength, but are generally incorporated with conventional biologically inert extenders or carriers normally employed for facilitating dispersion of active ingredients for agricultural chemical applications, recognizing the accepted fact that the formulation and mode of application may affect the activity of a material. The toxicants of this invention may be applied as sprays, dusts or granules to the insects, their environment or hosts susceptible to insect attack. They may be formulated as granules of large particle size, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from 5 80% toxicant and the rest inert material which includes dispersing agents, emulsifying agents, and wetting agents. The powder may be applied to the soil as a dry dust or preferably as a suspension in water. Typical carriers include fuller's earth, kaolin clays, silica, and other highly absorbent, readily wettable, inorganic diluents. Typical wetting, dispersing or emulsifying agents used in agricultural formaulations include, for example the alkyl and alkylaryl sulfonates and their sodium salts; alkylamide sulfonates, including fatty methyl taurides; alkylaryl polyester alcohols, sulfated higher alcohols, and polyvinyl alcohols; polyethylene oxides; sulfonate animal and vegetable oils; sulfonated petroleum oils; fatty acids esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1 to 15% by weight of the presticidal composition.

Dusts are freely flowing admixtures o the active ingredient with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogenous liquid or paste compositions which are readily dispersed in water or other dispersant, and may consist entirely of the toxicant with a liquid or solid emulsifying agent, or may also contain a liquid carrier, such as xylene, heavy aromatic naphthas, isophorone, and other non-volatile organic solvents. For applicantion these concentrates are dispersed in water or other liquid carrier, and are normally applied as a spray to the area to be treated.

Other useful formualtions for insecticidal applications include simple solutions of the active ingredient in a dispersant in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Baits, prepared by mixing solid or liquid concentrates of the toxicant with a suitable food, such as a mixture of cornmeal and sugar, are useful formulations for control of insect pests. Pressurized sprays, typically aerosols wherein the active ingredient is dispersed in finely divided form as a result of vaporization of a low-boiling dispersant solvent carrier, such as the freons, may also be used. All of these techniques for formulating and applying the active ingredient are well known in the art.

The percentages by eight of the toxicant may vary according to the manner in which the composition is to be applied and the particular type of formulation, but in general comprises 0.5 to 95% of the toxicant by weight of the pesticidal composition.

The pesticidal composition may be formulated and applied with other active ingredients, including other nematocides, insecticides, fungicides, bactericides, plant growth regulators, fertilizers, etc. In applying the chemical an effective amount and concentration of the toxicants of this invention is, of course, employed.

The terms "insecticide" and "insect" as used herein refer to their broad and commonly understood usage rather than to those creatures which in the strict biological sense are classified as insects. Thus, the term "insect" is used not only to include small invertebrate animals belonging to the class Insect, but also to other related classes of arthropods whose members are segmented invertebrates having or fewer than six legs such as spiders, mites, ticks, centipedes, worms, and the like.

What is claimed is:

1. Divalent calcium or barium salt of O, S-dialky-N-alkanoylphosphoroamidothioate wherein the O-alkyl and S-alkyl have 1 to 6 carbon atoms and the alky of the N-alkanoyl group has 1 to 18 carbon atoms.

2. The salt of claim 1 wherein the O-alkyl, S-alkyl and the alkyl of the N-alkanoyl group individually have 1 to 3 carbon atoms 3. The salt of claim 2 wherein the metal is calcium.

4. The salt of claim 1 represented by the formula

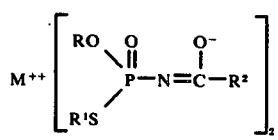

wherein M is calcium and R, R² and R² individually are alkyl of 1 to 3 carbon atoms.

5. The salt of claim 4 wherein R, R¹ and R² are methyl.

6. A mehtod of controlling insects which comprises applying to a solid insects, their environment or hosts an insecticidally effective amount of the salt of claim 1.

7. The method of claim 6 wherein the O-alkyl, S-alkyl and the alkyl of the N-alkanoyl group individually have 1 to 3 carbon atoms.

8. The method of claim 7 wherein the metal is calcium.

9. The method of claim 1 wherein the salt is represented by the formula

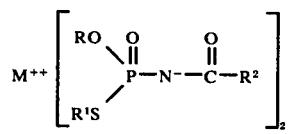

wherein M is a calcium and R R¹ and R² individually are alkyl of 1 to 3 carbon atoms.

10. The method of claim 9 wherein R, R² are methyl.

11. An insecticidal composition comprising an insecticidally effective amount of the compound claim 2 and a biologically inert carrier.

12. An insecticidal composition comprising an insecticidally effective amount of the compound of claim 2 and a biologically inert carrier.

13. An insecticidal composition comprising an insecticidally effective amount of the compound of claim 3 and a biologically inert carrier.

14. An insecticidal composition comprising an insectidally effective amount of the compound of claim 4 and a biologically inert carrier.

15. An insecticidal composition comprising an insecticidally effective amount of the compound of claim 5 and a biologically inert carrier.

* * * * *